United States Patent
Ludwig et al.

(10) Patent No.: US 9,179,926 B2
(45) Date of Patent: Nov. 10, 2015

(54) MINIMALLY INVASIVE SPINAL FIXATION GUIDE SYSTEMS AND METHODS

(75) Inventors: Steven Ludwig, Baltimore, MD (US); David Greg Anderson, Moorestown, NJ (US); Michael Carl Michielli, Medway, MA (US); Philip Cormier, Quincy, MA (US); Nicholas J. Miller, Taunton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 196 days.

(21) Appl. No.: 13/251,813

(22) Filed: Oct. 3, 2011

(65) Prior Publication Data
US 2012/0022599 A1 Jan. 26, 2012

Related U.S. Application Data

(63) Continuation of application No. 11/163,963, filed on Nov. 4, 2005, now Pat. No. 8,075,591.

(60) Provisional application No. 60/626,138, filed on Nov. 9, 2004.

(51) Int. Cl.
*A61B 17/88* (2006.01)
*A61B 17/90* (2006.01)
(Continued)

(52) U.S. Cl.
CPC ......... *A61B 17/1757* (2013.01); *A61B 17/7088* (2013.01); *A61B 17/1735* (2013.01); *A61B 17/7034* (2013.01)

(58) Field of Classification Search
CPC ............... A61B 17/70; A61B 17/7001; A61B 17/7002; A61B 17/7005; A61B 17/7007; A61B 17/7008; A61B 17/701; A61B 17/7011; A61B 17/7013; A61B 17/7014; A61B 17/7019; A61B 17/702; A61B 17/7022; A61B 17/7032; A61B 17/7034; A61B 17/7035; A61B 17/7037; A61B 17/7038; A61B 17/7041; A61B 17/7043; A61B 17/7046; A61B 17/1735; A61B 17/1757; A61B 17/7088
USPC ................................ 606/264–279, 86 A, 914
See application file for complete search history.

(56) References Cited

U.S. PATENT DOCUMENTS

| 4,733,657 A | 3/1988 | Kluger |
|---|---|---|
| 5,478,340 A | 12/1995 | Kluger |

(Continued)

FOREIGN PATENT DOCUMENTS

| AU | 2005304872 A1 | 5/2006 |
|---|---|---|
| CA | 2587011 A1 | 5/2006 |

(Continued)

OTHER PUBLICATIONS

"A New System for the Anterior Restoration and Fixation of Thoracic Spinal Deformities Using an Endoscopic Approach", SPINIE, vol. 25, No. 7, pp. 876-883, Apr. 1, 2000.

(Continued)

*Primary Examiner* — Michael T Schaper
*Assistant Examiner* — Tracy Kamikawa
(74) *Attorney, Agent, or Firm* — Nutter McClennen & Fish LLP

(57) ABSTRACT

Methods and devices that utilize segmental fixation between several adjacent vertebrae, thus allowing each vertebrae to be adjusted independently, are provided. In general, the device includes a spinal anchoring element that is adapted to seat at least one spinal fixation element, and a closure mechanism that is adapted to mate to the spinal anchoring element to lock the at least one spinal fixation element in a fixed position relative to the spinal anchoring element.

19 Claims, 19 Drawing Sheets

(51) Int. Cl.
*A61B 17/17* (2006.01)
*A61B 17/70* (2006.01)

(56) References Cited

U.S. PATENT DOCUMENTS

| | | | |
|---|---|---|---|
| 5,616,143 A * | 4/1997 | Schlapfer et al. | 606/86 A |
| 6,159,179 A | 12/2000 | Simonson | |
| 6,235,028 B1 | 5/2001 | Brumfield et al. | |
| 6,340,363 B1 | 1/2002 | Bolger et al. | |
| 6,475,218 B2 | 11/2002 | Gournay et al. | |
| 6,530,929 B1 | 3/2003 | Justis et al. | |
| 6,544,231 B1 | 4/2003 | Palmer et al. | |
| 6,648,888 B1 | 11/2003 | Shluzas | |
| 6,685,705 B1 | 2/2004 | Taylor | |
| 6,726,692 B2 | 4/2004 | Bette et al. | |
| 6,790,209 B2 | 9/2004 | Beale et al. | |
| 7,179,261 B2 | 2/2007 | Sicvol et al. | |
| 7,527,638 B2 | 5/2009 | Anderson et al. | |
| 7,648,507 B2 | 1/2010 | Techiera et al. | |
| 7,666,188 B2 | 2/2010 | Anderson et al. | |
| 8,075,591 B2 | 12/2011 | Ludwig et al. | |
| 2002/0013585 A1 | 1/2002 | Gournay et al. | |
| 2002/0068975 A1* | 6/2002 | Teitelbaum et al. | 623/17.11 |
| 2002/0095153 A1 | 7/2002 | Jones et al. | |
| 2002/0123668 A1 | 9/2002 | Ritland | |
| 2002/0161368 A1 | 10/2002 | Foley et al. | |
| 2003/0060826 A1 | 3/2003 | Foley et al. | |
| 2003/0083688 A1 | 5/2003 | Simonson | |
| 2003/0083689 A1 | 5/2003 | Simonson | |
| 2003/0187431 A1 | 10/2003 | Simonson | |
| 2003/0208203 A1* | 11/2003 | Lim et al. | 606/61 |
| 2003/0236447 A1 | 12/2003 | Ritland | |
| 2004/0039384 A1 | 2/2004 | Boehm et al. | |
| 2004/0106921 A1 | 6/2004 | Cheung et al. | |
| 2004/0106997 A1* | 6/2004 | Lieberson | 623/17.16 |
| 2004/0172020 A1 | 9/2004 | Beaurain et al. | |
| 2004/0172022 A1 | 9/2004 | Landry et al. | |
| 2005/0038436 A1 | 2/2005 | Michelson | |
| 2005/0065517 A1 | 3/2005 | Chin | |
| 2005/0080418 A1 | 4/2005 | Simonson et al. | |
| 2005/0085813 A1 | 4/2005 | Spitler et al. | |
| 2005/0131421 A1 | 6/2005 | Anderson et al. | |
| 2005/0131422 A1 | 6/2005 | Anderson et al. | |
| 2005/0154389 A1 | 7/2005 | Selover et al. | |
| 2005/0192589 A1 | 9/2005 | Raymond et al. | |
| 2005/0209694 A1* | 9/2005 | Loeb | 623/17.11 |
| 2005/0215999 A1 | 9/2005 | Birkmeyer et al. | |
| 2005/0234451 A1* | 10/2005 | Markworth | 606/61 |
| 2006/0030839 A1* | 2/2006 | Park et al. | 606/1 |
| 2006/0064099 A1 | 3/2006 | Pavlov et al. | |
| 2006/0084978 A1 | 4/2006 | Mokhtar | |
| 2007/0055291 A1 | 3/2007 | Birkmeyer et al. | |

FOREIGN PATENT DOCUMENTS

| | | |
|---|---|---|
| DE | 2649042 B1 | 1/1978 |
| DE | 10027988 A1 | 1/2002 |
| EP | 0553782 A1 | 8/1993 |
| EP | 1820114 A2 | 8/2007 |
| JP | 2007532258 T | 11/2007 |
| JP | 2008519611 T | 6/2008 |
| WO | 2005104970 A1 | 11/2005 |

OTHER PUBLICATIONS

International Search Report and Written Opinion dated Sep. 16, 2008 for PCT/US08/59889.
European Search Report for EP No. 05 81 7489, Nov. 11, 2009 (8 pages).
International Search Report, Sep. 13, 2007, International Application No. PCT/US05/40158.
Australian first Examiner Report for applicaiton No. 2005304872, dated May 5, 2008, 2 pages.
Japanese Office Action for JP 2007-540104, dated Apr. 12, 2011, 11 pages.
Japanese Office Action dated Apr. 3, 2012 for Application No. 2007-540104. (6 pages).

* cited by examiner

MINIMALLY INVASIVE SPINAL FIXATION GUIDE SYSTEMS AND METHODS

CROSS REFERENCE TO RELATED APPLICATIONS

The present application is a continuation of U.S. patent application Ser. No. 11/163,963 (now U.S. Pat. No. 8,075, 591) filed on Nov. 4, 2005 and entitled "Minimally Invasive Spinal Fixation Guide Systems and Methods," which claims priority to U.S. Provisional Patent Application No. 60/626, 138 filed on Nov. 9, 2004 and entitled "Minimally Invasive Spinal Fixation Guide Systems and Methods." These references are hereby incorporated by reference in their entireties.

BACKGROUND OF THE INVENTION

For a number of known reasons, spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation elements can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism is used to lock the fixation element, e.g., a spinal rod, into the rod-receiving head of the pedicle screw. In use, the shank portion of each screw is threaded into a vertebra, and once properly positioned, a rod is seated through the rod-receiving member of each screw and the rod is locked in place by tightening a cap or other fastener mechanism to securely interconnect each screw and the fixation rod.

Recently, the trend in spinal surgery has been moving toward providing minimally invasive devices and methods for implanting spinal fixation devices. One such method, for example, utilizes two percutaneous access devices for implanting an anchoring device, such as a spinal screw, into adjacent vertebrae. A spinal rod is then introduced through a third incision a distance apart from the percutaneous access sites, and the rod is transversely moved into the rod-engaging portion of each spinal screw. The percutaneous access devices can then be used to apply closure mechanisms to the rod-engaging heads to lock the rod therein. While this procedure offers advantages over prior art invasive techniques, the transverse introduction of the rod can cause significant damage to surrounding tissue and muscle.

Accordingly, there remains a need for improved methods and devices for introducing spinal fixation elements, spinal anchors, and/or other spinal devices into a patient's spine.

SUMMARY OF THE INVENTION

Disclosed herein are methods and devices for implanting spinal fixation implants and devices. In one exemplary embodiment, a method for implanting a spinal fixation system includes positioning a spinal fixation element to extend along a patient's spinal column adjacent to one or more vertebrae, determining an implant site on at least one vertebra, and implanting at least one spinal anchor at the implant site on at least one vertebra. In an exemplary embodiment, the spinal fixation element may be inserted through a first incision, and each spinal anchor may be inserted through an incision separate from the spinal fixation element and one another. Once the spinal anchor(s) are implanted, the spinal fixation element may be moved, e.g., approximated, toward the spinal anchor(s) to couple, statically or dynamically, the spinal fixation element to the anchor(s). In one exemplary method, the spinal fixation element may be locked to the spinal anchor(s) to maintain the vertebrae in a fixed position relative to one another. In other exemplary embodiments, one or more of the spinal anchors may be dynamically coupled to the spinal fixation element to permit movement of one or more vertebrae relative to other vertebrae.

Further disclosed herein are various exemplary techniques for positioning the spinal fixation element along the patient's spinal column. In one embodiment, the spinal fixation element may be introduced through a cannula or port and manipulated to position the fixation element such that it extends along the patient's spinal column. An insertion tool, such as a pivoting implant holder, can be used to introduce the spinal fixation element through an incision or through a cannula or port. The insertion tool may be effective to insert the spinal fixation element in a first orientation and to pivot the spinal fixation element into a second orientation in which the spinal fixation element is substantially parallel to a patient's spinal column.

Also disclosed herein are various techniques for determining an implant site on each vertebra. In one exemplary embodiment, a targeting member may be positioned relative to a target implant site on a vertebra, and the targeting member may be aligned relative to the target implant site using an imaging device. The targeting member may be part of a guide system having a guide portion that is adapted to be positioned outside a patient's body and to extend along a patient's spinal column, and a rod-engaging member that is adapted to couple to the spinal fixation element to maintain the spinal fixation element in a fixed position within the patient's body extending adjacent to a patient's spinal column. The targeting members may be slidably disposed on the guide portion to allow each targeting member to be adjusted relative to a target implant site on a vertebra.

Various techniques for implanting the spinal anchor(s) are also disclosed herein. In one exemplary embodiment, one or more spinal anchors can be percutaneously delivered to the anchor site through a cannula which may be positioned through a minimally invasive pathway to the spinal anchor site. Each cannula may be attached to a guide system that is adapted to couple to the spinal fixation element. In other exemplary embodiments, the spinal anchors can be delivered through an access port that defines a large working channel.

Techniques for coupling the fixation element to the anchor(s) are disclosed herein. In one exemplary embodiment, the spinal fixation element may be moved, e.g., approximated, toward the spinal anchor(s) by engaging the spinal fixation element and a spinal anchor with a grasping tool. In certain exemplary embodiments, one or more of the spinal anchors may be a side-loading, top-tightening spinal anchor to allow the fixation element to be approximated into a side-opening in an anchor and to allowed a locking mechanism to be introduced into the top of the anchor to lock the fixation element within the anchor.

In yet another exemplary embodiment, a surgical method includes inserting a spinal rod through a first incision to position the spinal rod adjacent to a plurality of vertebrae in a patient's spinal column, determining an implant site on each vertebra, making a percutaneous incision at the implant site on each vertebra, creating a pathway from the percutaneous incision to the implant site on each vertebra, placing an anchor through each pathway to implant an anchor in each vertebra, approximating the spinal rod toward the anchors, and locking the spinal rod to each anchor.

Further disclosed herein are guide systems for use in spinal surgery. In one exemplary embodiment, an exemplary guide system includes a guide portion that is adapted to be positioned outside a patient's body and to extend along a patient's spinal column, a rod-engaging member that is mated to the guide portion and that is adapted to couple to a spinal rod and to maintain the spinal rod in a fixed position within the patient's body extending adjacent to a patient's spinal column, and one or more targeting member that are slidably coupled to the guide portion. The targeting member may be adapted to target an implant site on a vertebra in the patient's spinal column. The targeting members can be removably coupled to a support member that is slidably disposed on the guide portion, and each support member can also be configured to mate to a cannula for providing a pathway to an implant site.

While the guide system can have a variety of configurations, in one embodiment the rod-engaging member is effective to maintain the rod in a fixed position that is spaced a distance apart from the guide portion and substantially parallel to the guide portion. The targeting member may be adapted to target an implant site on a vertebra that is at a location offset from the spinal rod. In other exemplary embodiments, the device can include a locking mechanism coupled to the rod-engaging member and effective to removably mate a spinal fixation rod to the rod-engaging member.

In yet another exemplary embodiment, a guide system for use in spinal surgery includes a guide member having a rod-engaging portion that is adapted to maintain a spinal fixation element at a fixed position in a patient's body that is substantially parallel to the guide member, and at least one targeting element that is adapted to target an implant site on a vertebra at a location that is offset from the spinal fixation element.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Disclosed herein are methods and devices for introducing spinal fixation elements, spinal anchors, and/or other spinal devices into a patient's spine. A person skilled in the art will appreciate that, while the methods are described in connection with certain spinal instruments and devices, a variety of spinal instruments and devices can be used to perform the methods in accordance with the various embodiments disclosed herein. Conversely, the instruments and devices disclosed herein can be used for a variety surgical procedures. Moreover, a person skilled in the art will appreciate that exemplary methods can be performed in any sequence using only some or all of the methods.

Figure 1:
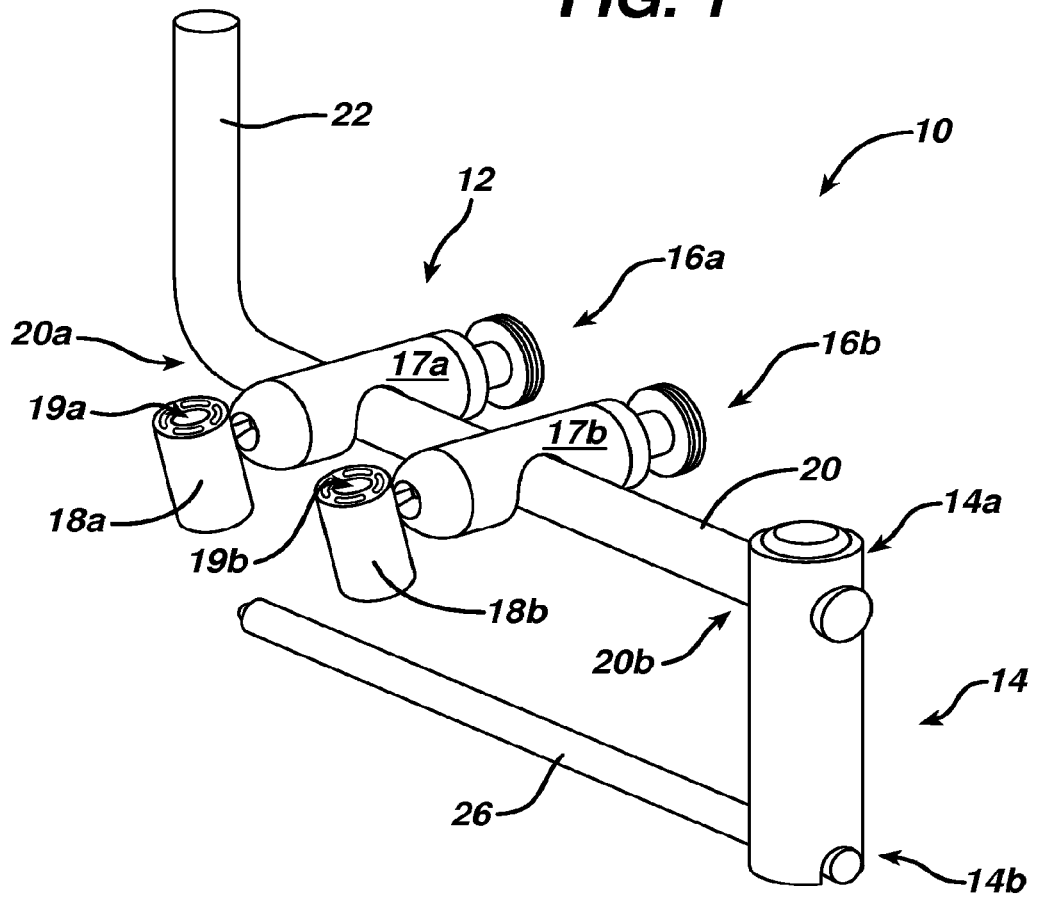
FIG. 1 is a perspective view of an exemplary guide system for implanting a spinal fixation element and one or more spinal anchors.

FIG. 1 illustrates an exemplary embodiment of a guide system 10 that can be used to position a spinal fixation element, such as a spinal rod, a plate, and/or a cable or tether, in a patient's spinal column, to target implant sites on one or more vertebra, and, in certain exemplary embodiments, to facilitate implanting a spinal anchor in a vertebra. As shown, the guide system 10 generally includes a guide portion 12 that is adapted to be positioned outside a patient's body and a rod-engaging portion 14 that is adapted to couple to a spinal fixation element, such as spinal rod 26, to maintain the spinal rod 26 in a fixed position within the patient's body such that the rod 26 extends adjacent to a patient's spinal column. The rod-engaging portion 14 may be effective to maintain the spinal rod 26 in a position that is substantially parallel to, but spaced apart from, the guide portion 12 such that guide portion 12 serves as a guide located outside of the body to indicate the location of the spinal rod 26 disposed inside the patient's body. The guide system 10 can also include one or more targeting instruments 16a, 16b that are movably coupled to the guide portion 12 of the system 10. The targeting instruments 16a, 16b can be adapted to target an implant site on a vertebra in the patient's spinal column.

The guide portion 12 of the guide system 10 can have a variety of configurations. In one embodiment, for example, the guide system 10 is effective to indicate the position of a spinal rod 26 disposed within and extending along a patient's spinal column. As shown in FIG. 1, the guide portion 12 has a generally elongate support rod 20 with opposed first and second ends 20a, 20b. The first end 20a can include a handle 22 formed thereon or mated thereto for facilitating grasping and manipulation of the system 10. The handle 22 can also optionally be used to couple the guide system 10 to a support, such as a table. The second end 20b may be adapted to couple to the rod-engaging portion 14. The rod-engaging portion 14 can have virtually any shape and size. For example, in the illustrated embodiment, the rod engaging portion 14 extends in a direction that is transverse to the support rod 20 and it is adapted to removably engage a spinal rod 26. As shown in FIG. 1, the first end 14a of the rod-engaging portion 14 may be mated to the second end 20b of the support rod 20, and the second end 14b of the rod-engaging portion 14 is in engagement with a spinal rod 26. While not illustrated, virtually any technique can be used to removably engage a spinal rod 26, including, for example, a clamping mechanism, a threaded engagement, an interference fit, etc. Some exemplary techniques for engaging a spinal rod will be discussed in more detail below with respect to FIGS. 3A-3B. The rod-engaging portion 14 can also include a locking mechanism (not shown) for locking the spinal rod 26 relative to the rod-engaging portion 14, and for subsequently releasing the rod 26 from the rod-engaging portion 14.

The guide system 10 can also include one or more targeting instruments coupled thereto. As shown in FIG. 1, two targeting instruments 16a, 16b are slidably disposed on the support rod 20 of the guide portion 12. While a variety of targeting instruments and techniques can be employed, in an exemplary embodiment, as shown, one or more of the targeting instruments 16a, 16b may include a slidable support 17a, 17b and a targeting member 18a, 18b coupled to a terminal end of the support 17a, 17b. The targeting members 18a, 18b may be positioned a distance apart from the support rod 20 as illustrated or at other positions relative to the support rod 20. Spacing the targeting members 18a, 18b apart from the support rod 20 allows the targeting members 18a, 18b to target an implant site on the vertebrae without interference from the spinal rod 26, which is located adjacent to the spinal column. In certain exemplary embodiments, the targeting members 18a, 18b may be movably coupled to the supports 17a, 17b such that the targeting members 18a, 18b can be moved toward and away from the supports 17a, 17b, as well as angularly adjusted relative to the supports 17a, 17b. Such a configuration allows the targeting instrument 18a, 18b to be properly aligned with a target implant site on a vertebra. While one embodiment for targeting members 18a, 18b can be angularly adjustable, one skilled in the art will appreciate that the members can also be mounted at a fixed angle. Although not illustrated, guide portion 12 can initially be attached to rod-engaging portion 14 such that it extends in a direction opposite to that shown in FIG. 1 during rod insertion. This configuration can provide enhanced visibility and maneuverability during rod insertion. Alternatively, a handle (not shown) can be connected to first end 14a of rod-engaging portion 14 during rod insertion, and the handle can subsequently be replaced with guide portion 12.

Figure 9:
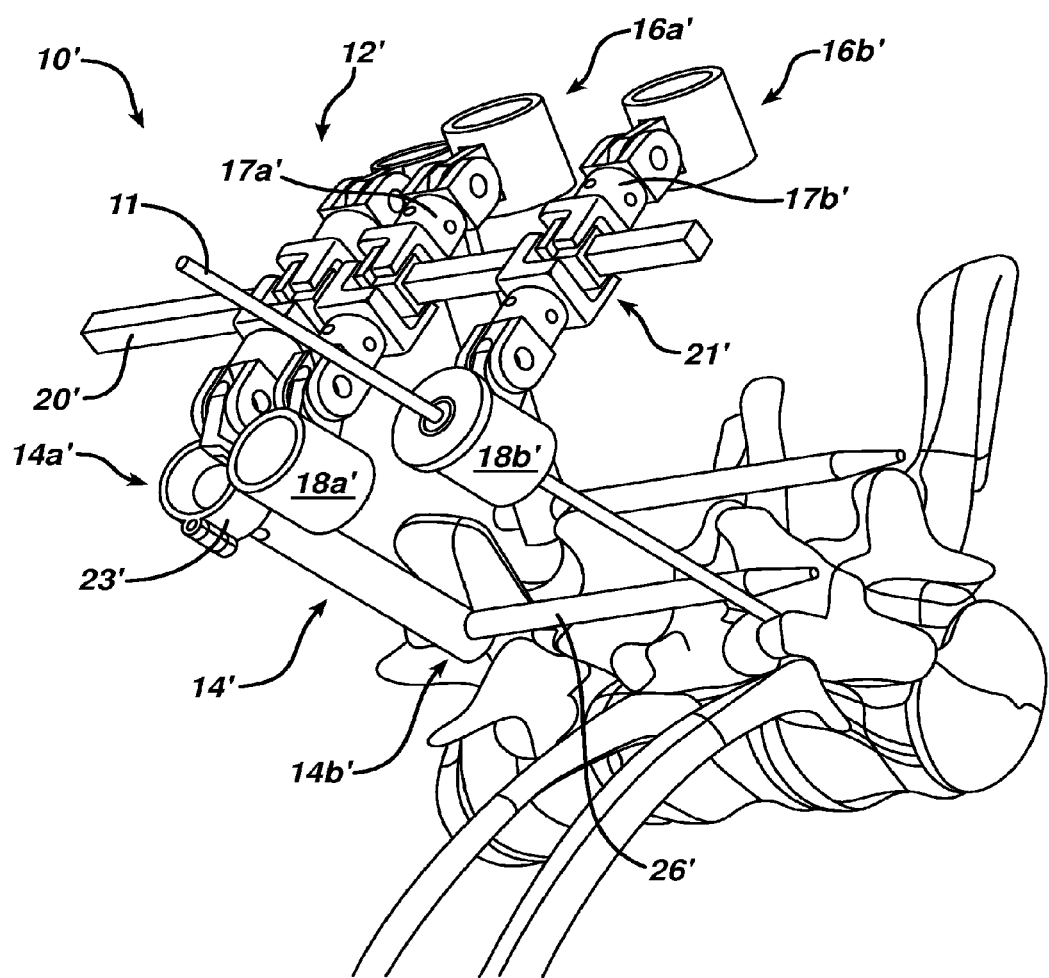
FIG. 9 is a perspective view of another exemplary embodiment of a guide system for implanting a spinal fixation element and one or more spinal anchors.
Figure 10:
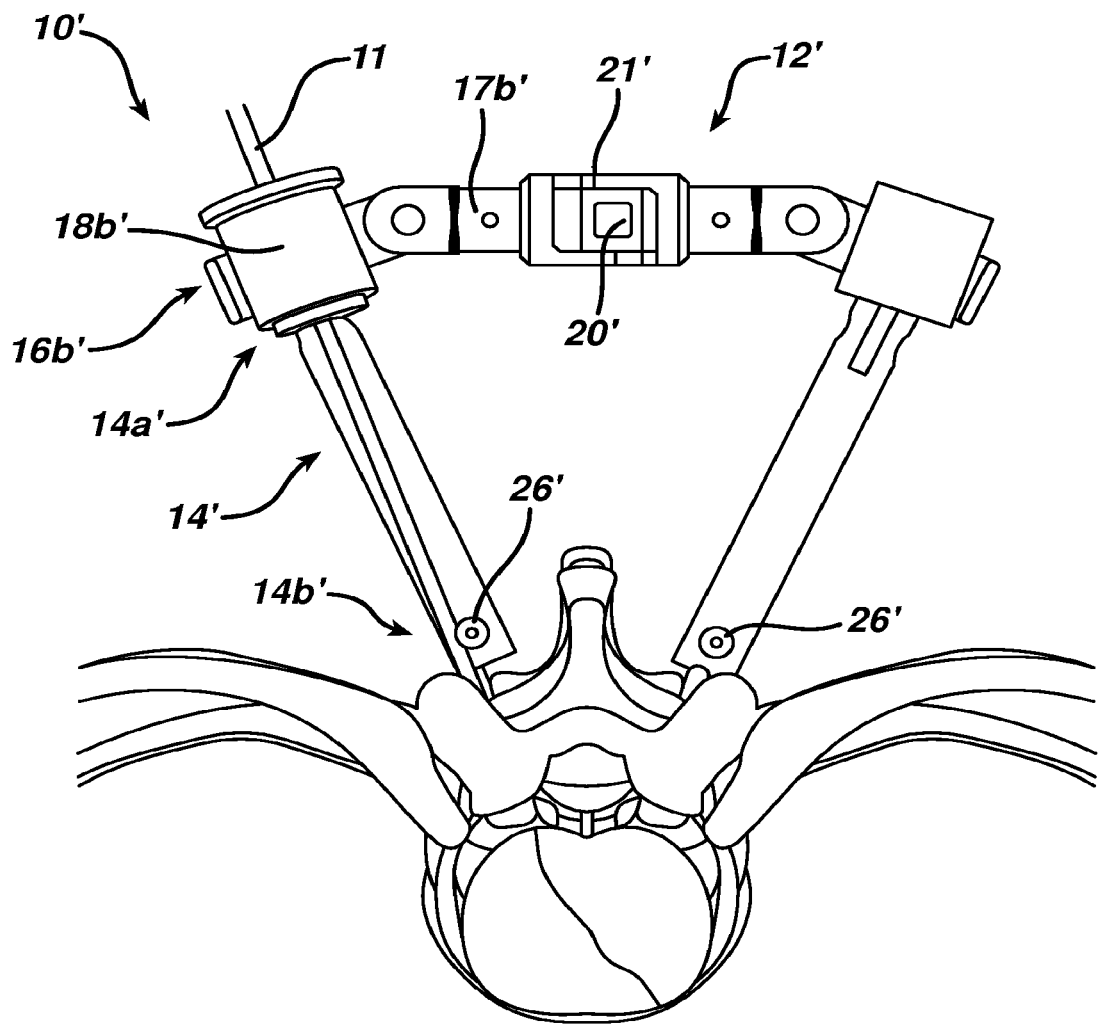
FIG. 10 is an end view of the guide system shown in FIG. 9.

FIGS. 9 and 10 illustrate another embodiment of a guide system 10' that can be used to position a spinal fixation element, such as a spinal rod, a plate, and/or a cable or tether, in a patient's spinal column, to target implant sites on one or more vertebra, and in certain exemplary embodiments, to facilitate implanting a spinal anchor in a vertebra. Similar to the system 10 shown in FIG. 1, the guide system 10' of FIGS. 9 and 10 provide further adjustability options and it generally includes a guide portion 12' that is adapted to be positioned outside a patient's body and a rod-engaging portion 14' that is adapted to couple to a spinal fixation element, such as a spinal rod 26', to maintain the spinal rod 26' in a fixed position within the patient's body such that the rod 26' extends adjacent to a patient's spinal column. The rod-engaging portion 14' may be effective to maintain the spinal rod 26' in a position that is substantially parallel to, but spaced apart from, the guide portion 12' such that guide portion 12' serves as a guide located outside of the body to indicate the location of the spinal rod 26' disposed inside the patient's body. The guide system 10' can also include one or more targeting instruments 16a', 16b' that are movably coupled to the guide portion 12' of the system 10'. The targeting instruments 16a', 16b' can be adapted to target an implant site on a vertebra in the patient's spinal column.

Many components of the guide system 10', including support rod 20', rod-engaging portion 14', and rod 26', are similar to corresponding components discussed above with respect to guide system 10. However, the guide system 10' enables adjustment with additional degrees of freedom, and it is somewhat differently constructed. While the system 10, shown in FIG. 1, utilizes rod-engaging portion 14 in such a way that it extends directly between rod 26 and support rod 20, the guide system 10' illustrated in FIGS. 9 and 10 indirectly connects the support rod 20' and the rod-engaging portion 14'. That is, one end 14b' of the rod-engaging portion 14' attaches to rod 26' while the other end 14a' is removably engaged in one of the targeting instruments 16a', 16b', such as by sleeve 23'. The targeting instrument to which rod-engaging portion 14' is attached is connected to support rod 20' by way of slidable support 17a', 17b' as shown in FIGS. 9 and 10. Such a design enables effective targeting without requiring alignment of support rod 26' with rod 20'. For example, a k-wire 11 can be inserted through the targeting members 18a', 18b' at a wide angle. Further, k-wire 11, if used, can be manipulated in such a way that it is rotated relative to the rod 26' to provide multiple screw trajectories relative to the rod in order to achieve the proper relationship between the screw trajectory and the rod.

One skilled in the art will appreciate that a variety of connector mechanisms can be used to mate rod-engaging portion 14' to rod 26' and targeting instrument 16a', 16b'.

Further adjustability of the guide system 10' is provided by the embodiment illustrated in FIGS. 9 and 10 by supports 17a', 17b', which have targeting members 18a', 18b' coupled to terminal ends thereof. Similar to the embodiment shown in FIG. 1, the guide system 10' shown in FIGS. 9 and 10 has a slidable support 17a', 17b' that can be moved along the longitudinal axis of the support rod 20'. In addition, the support 17a', 17b' can move (such as by a telescoping movement) in a direction transverse (i.e., laterally) to the support rod 20'. As shown in FIGS. 9 and 10, the targeting members 18a', 18b' may be positioned a selected distance apart from the support rod 20' thereby allowing the targeting members 18a', 18b' to target an implant site on the vertebrae without interference from the spinal rod 26'. Additionally, as in the embodiment illustrated in FIGS. 9 and 10, the targeting members 18a', 18b' can be angularly adjusted in the cephalad-candal direction and/or in the medial-lateral direction, such as by rotating supports 17a', 17b' about an axis transverse to rod support 20'.

The guide system 10' may also include gauges and/or indicia (not shown) to indicate angular and/or other spatial positioning of the various adjustable components of guide portion 12' with respect to a reference, such as support rod 20'. These features can be useful, for example, to construct a system with a preset positioning for one or more levels of the spine that may be subject to surgery. The preset positioning can be established based on preoperative data (e.g., CT data) or anatomic data derived from a population sample. A surgeon could use the preset positioning of the guide system, if appropriate, or minor adjustments can be made to the preset positioning based on the needs of a patient.

While the targeting members 18a, 18b, 18a', 18b' can have a variety of configurations, U.S. Publication No. 2003/0187431 of Simonson entitled "Apparatus and Method for Targeting for Surgical Procedures," which is incorporated by reference herein in its entirety, discloses one such device for targeting an implant site. A person skilled in the art will appreciate that a variety of techniques and devices for targeting an implant site can be used with the present invention.

The targeting instruments 16a, 16b, 16a', 16b' can also be configured to facilitate use of the guide system 10, 10' with other spinal tools and devices. For example, the targeting members 18a, 18b, 18a', 18b' can include an inner lumen 19a, 19b extending therethrough for receiving spinal tools and devices, such a drill guides, cannulas, and access ports. Alternatively, or in addition, the targeting members 18a, 18b, 18a', 18b' can be removably mated to the slidable support 17a, 17b, 17a', 17b' to allow each support member 17a, 17b, 17a', 17b' to mate to a cannula, access port, or other device or tool after the targeting members 18a, 18b, 18a', 18b' are removed. Each support 17a, 17b, 17a', 17b' can thus be used to maintain a cannula, access port, or other device in a fixed positioned relative to a target implant site, thereby providing a guided pathway to a target implant site on a vertebra, as will be discussed in more detail below. One skilled in the art will appreciate that they system 10, 10' can be configured for unilateral rod placement or for bilateral rod placement as shown in FIGS. 9 and 10.

As previously noted, also disclosed herein are methods for implanting a spinal fixation system. While the method will be described in connection with guide system 10, 10', a person skilled in the art will appreciate that the method is not intended to be limited to use with guide system 10, 10' and that a variety of other devices can be used to perform the method. In general, an exemplary method includes positioning a spinal fixation device, such as the spinal rod 26, 26', to extend along a patient's spinal column adjacent to several vertebrae, targeting an implant site on vertebrae, implanting a spinal anchor in one or more vertebrae, and coupling a spinal rod to one or more spinal anchors. Various exemplary techniques for performing the aforementioned various steps are discussed below under the following headings: Rod Introduction, Targeting, Implanting Spinal Anchors, and Rod Approximation.

Rod Introduction

A variety of techniques can be used to position a spinal rod to extend along a patient's spinal column adjacent to two or more vertebrae, and the spinal rod can be introduced at various locations along the patient's spine. For example, the spinal rod can be introduced through the same incision used to introduce a spinal anchor, or alternatively the spinal rod can be introduced through an incision that is separate from and located a distance apart from the incision(s) used to implant the spinal anchor(s). The rod can also either be directly introduced through the incision to extend up along the patient's spinal column, or it can be introduced through a cannula, access port, or other device for guiding the rod to extend along the patient's spinal column. Various tools can also be coupled to the rod to manipulate and facilitate introduction and positioning of the rod in the patient's body.

In one exemplary embodiment, referring to FIGS. 1 and 9, the rod 26, 26' is attached to the guide system 10, 10' and the guide system 10, 10' is manipulated to insert the rod 26, 26' through an incision and to bluntly advance the rod 26, 26' through the soft tissue until the rod 26, 26' extends along the patient's spinal column, preferably adjacent to the pedicles. The proper position of the rod 26, 26' can be determined using fluoroscopy. Once properly positioned, the guide system 10, 10' is preferably fixedly attached to a support, such as the operating table, using, for example, a retractor arm.

Figure 2A:
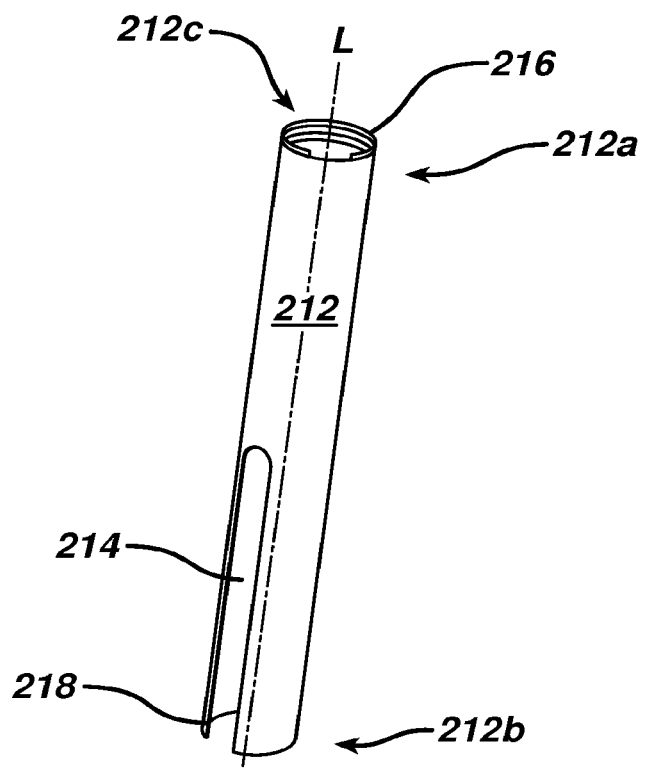
FIG. 2A is a side perspective view of an exemplary embodiment of a guide cannula for use with the methods and devices disclosed herein.

In another exemplary embodiment, the rod can be introduced through a cannula. FIG. 2A illustrates an exemplary embodiment of a cannula 212 for introducing a spinal fixation element, such as a rod. As shown, the cannula 212 is in the form of a generally elongate, cylindrical tube having an inner lumen 212c formed therein and defining a longitudinal axis L that extends between proximal and distal ends 212a, 212b thereof. The cannula 212 has a length/that allows the proximal end 212a of the cannula 212 to be positioned outside the patient's body, while the distal end 212b of the cannula 212 extends into the patient's body to define a pathway for the rod. The cannula 212 also includes at least one sidewall opening or slot 214, and more preferably two opposed sidewall openings (only one opening 214 is shown), formed therein and extending proximally from the distal end 212b thereof. The openings 214 allow the spinal rod to be rotated from a position coaxial with the cannula 212 to a position in which the rod extends along the spinal column.

Figure 2B:
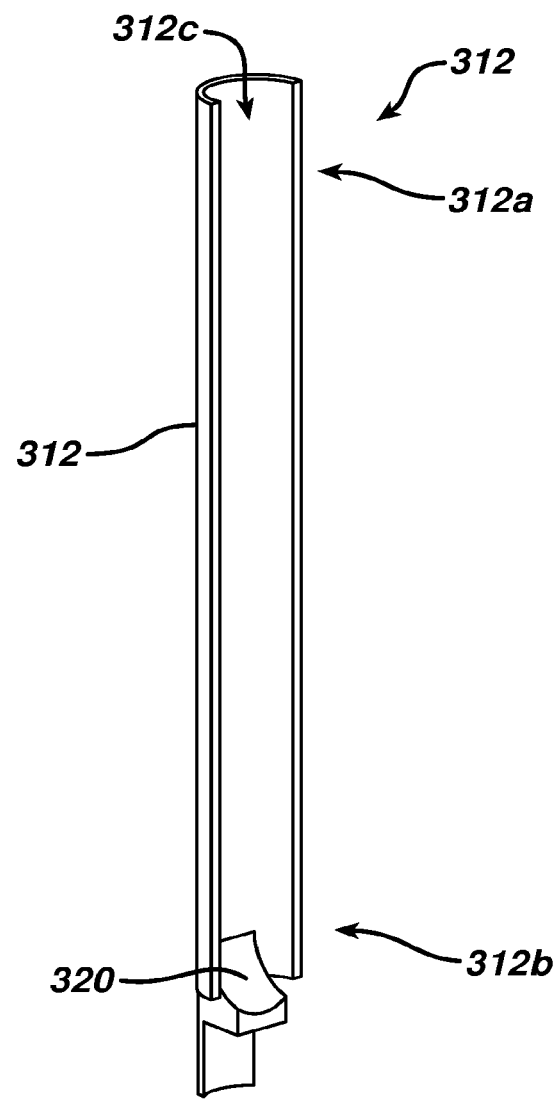
FIG. 2B is a cross-sectional, perspective view of another exemplary embodiment of a guide cannula for use with the methods and devices disclosed herein.

In another embodiment, shown in FIG. 2B, an exemplary cannula 312 can include a guide member 320 formed within the distal end 312b of the lumen 312c to help guide the spinal rod from the first orientation to the second orientation. The guide member 320 is in the form of a sloped shelf formed within the inner lumen 312c of the cannula 312 and it is positioned opposite to a sidewall slot 314 formed in the access device 312. In use, as the leading end of a spinal rod contacts the shelf 320 and the shelf 320 begins to direct the spinal rod into the second orientation, thereby causing the spinal rod to extend in a direction that is substantially transverse to the axis L of the device 312, and that is preferably substantially parallel to the patient's spinal column.

Other exemplary techniques for introducing a spinal rod through a cannula or access device and into a patient's body are described in more detail in U.S. patent application Ser. No. 10/738,130 of Anderson et al. entitled "Methods And Devices For Minimally Invasive Spinal Fixation Element Placement," and U.S. patent application Ser. No. 10/737,537 of Anderson et al. entitled "Methods And Devices For Spinal Fixation Element Placement." These references are incorporated by reference herein in their entirety.

Figure 3A:
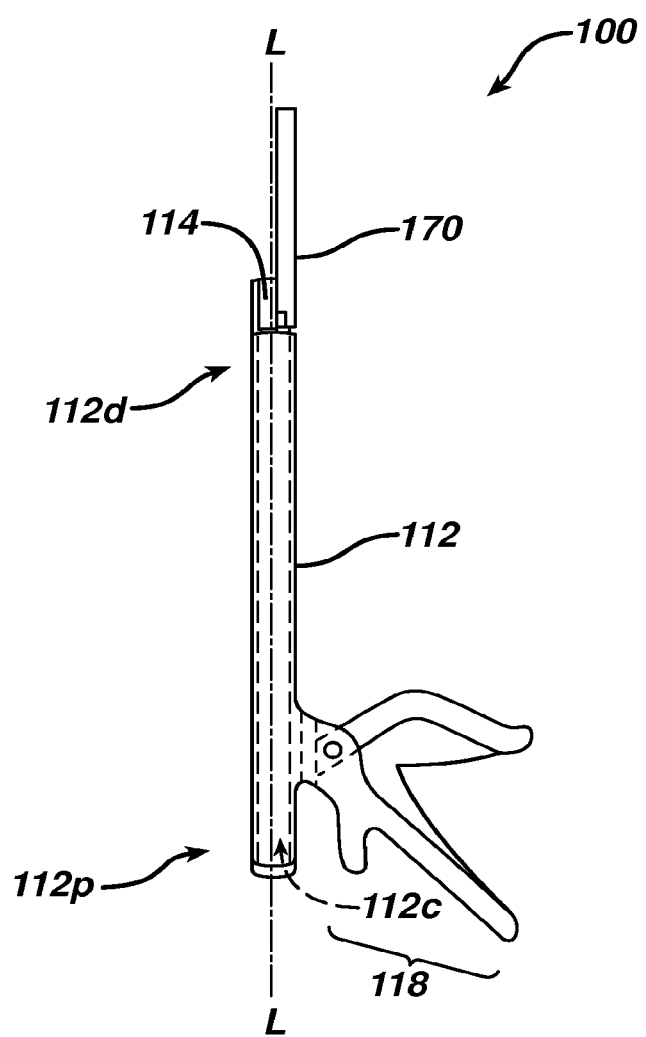
FIG. 3A is a side view of an exemplary pivoting implant holder having a spinal fixation element mated thereto and positioned in a first orientation adapted for introduction into a patient's spinal column.
Figure 3B:
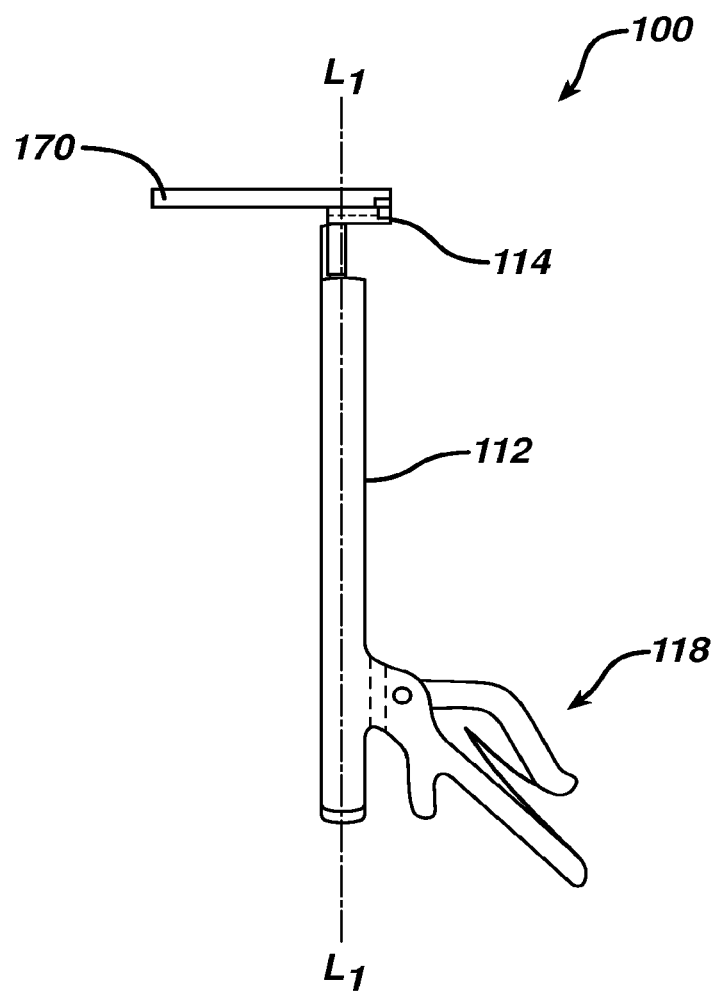
FIG. 3B is a side view of the pivoting implant holder shown in FIG. 3A with a spinal fixation element pivoted into a second orientation.

FIGS. 3A and 3B illustrate another exemplary embodiment of a technique for introducing a spinal fixation rod to position the rod to extend along the patient's spinal column. In particular, tool 100 can be used to engage a spinal rod and introduce the rod through a cannula or an access port, directly through an incision, or through other devices known in the art. As shown, the tool 100 generally includes an elongate shaft 112 having proximal and distal ends 112p, 112d with an inner lumen 112c extending therebetween. A pusher shaft (not shown) extends through the elongate shaft 112 and it preferably includes a proximal end that is coupled to a trigger 118, and a distal end that is coupled to a pivoting element 114. The trigger 118 functions to move the pusher shaft and thereby rotate a rod 170 coupled to the pivoting element 144 between a first orientation, in which the rod 170 is substantially coaxial with the longitudinal axis L' of the shaft 112, as shown in FIG. 3A, and a second orientation, in which the rod 170 extends in a direction transverse to the elongate shaft 112, as shown in FIG. 3B. The tool 100 can also include a mechanism for removably engaging the rod 170 to allow the rod 170 to be subsequently released from the tool 100 after it is disposed in the patient's body.

In use, the rod 170 is engaged by the tool and it is introduced through an access port or an incision in the first orientation shown in FIG. 2A. The trigger 118 can then be engaged to rotate or pivot the rod 170 into the second orientation, shown in FIG. 2B, thereby positioning the rod substantially parallel to the patient's spinal column. The rod 170 can then be released from the tool 100 and attached to the rod-engaging member 14, 14' of the guide system 10, 10'. In an alternative embodiment, the tool 170, or a variation of the tool 170, can be formed integrally with the guide system 10, 10' such that the tool 170 functions as the rod-engaging member.

The tool 100, and other embodiments of tools for introducing a spinal rod, are described in more detail in U.S. patent application Ser. No. 10/737,538 of Techiera et al. filed on Dec. 16, 2003 and entitled "Pivoting Implant Holder," which is incorporated by reference herein in its entirety. This patent application also discloses techniques for engaging a spinal fixation element, and such techniques can optionally be incorporated into system 10, 10' to couple a spinal rod to the rod-engaging member 14, 14'.

Regardless of the technique used to position the rod within the patient's body, the rod may be attached to the guide system 10, 10' which is maintained in a fixed position, e.g., by attaching the guide system to a support, such as the operating table. The rod can thereafter optionally be used to facilitate targeting of the implant sites.

Targeting

Once the rod is in place and attached to the guide system 10, 110', the targeting instruments can be used to identify a target implant site on one or more vertebrae. In particular, an imaging device can be placed over the targeting members 18a, 18b, 18a', 18b' to align the targeting members 18a, 18b, 18a', 18b' with the target implant sites on the underlying vertebra. Once aligned, the targeting members 18a, 18b, 18a', 18b' may be locked in place relative to the support 20, 20' on the guide system 10, 10'. The surgeon can then mark the incision location on the skin below the targeting members 18a, 18b, 18a', 18b'. Alternatively, a further incision is not needed, and targeting and pedicle screw insertion can be effected through the incision through which the rod is placed. As previously noted, exemplary methods and devices for targeting an implant site are described in more detail in U.S. Publication No. 2003/0187431 of Simonson entitled "Apparatus and Method for Targeting for Surgical Procedures," which is incorporated by reference herein in its entirety.

Once the implant sites on the vertebrae are targeted, the targeting members 18a, 18b, 18a', 18b' can remain attached to the guide system 10, 10' to allow tools and devices to be inserted through the lumens 19a, 19b formed therethrough, or they can be removed from the guide system 10, 10' to allow other tools and devices to be attached to the guide system 10, 10'.

Implanting Spinal Anchors

Once the target implant sites are identified, a spinal anchor can be implanted at one or more implant sites. Any type of conventional spinal anchor can be used to couple a rod, statically or dynamically, to one or more vertebrae. For illustration purposes, however, exemplary methods will be described in connection with a spinal screw, which can be a mono-axial screw or a poly-axial screw.

In one exemplary embodiment, the spinal anchor can be adapted to receive the spinal rod laterally. In particular, the spinal anchor can be a side-loading anchor, such that the rod can be pulled into an opening in the side of the anchor receiver head. FIGS. 5A, 5B, 6B, 7A, 7C, 7D and 8 illustrate an exemplary embodiment of a side-loading spinal screw 50 having an opening or rod-receiving recess 56 formed in a side of the receiver head 52 of the anchor 50. The rod-receiving recess 56 allows a rod to be laterally approximated into the receiver head 52, and/or it allows the receiver head 52 to be moved to position the rod within the opening 56. The rod can be locked within the receiver head 52 by inserting a locking mechanism into the top of the receiver head 52, thereby clamping down on the rod. FIG. 7B illustrates another embodiment of a side-loading spinal screw 80 having a threaded shaft 84 and a receiver head 82. In this embodiment, the receiver head 82 includes a rod-receiving recess 86 that is offset from an axis A of the screw 80, such that the rod is maintained at a location offset from the screw 80. In one exemplary embodiment, the rod-receiving recess 86 may be open in a lateral direction to facilitate capture of the rod within the rod receiving recess 86 as the screw 80 is advanced into the vertebra. The threaded shaft 84 of the screw 80 may include a head 85 that is free to rotate relative to the receiver head 82 such that the threaded shaft 84 may be polyaxially oriented relative to the receiver head 82, for example, in a manner analogous to conventional polyaxial screws. A locking mechanism, such as a set screw, for example, may be inserted into the receiver head to lock the head 85 of the threaded shaft 84 relative to the receiver head 82. A second locking mechanism, such as a second set screw, may be inserted to secure the rod in the rod receiving recess 86. In this manner, the head 85 of the shaft 84 may be locked independent of locking the rod within the recess 86. One skilled in the art will appreciate that such a system enables the position of vertebral bodies to be adjusted (e.g., in compression or distraction) by moving screws 50, 80 along rod 26. By way of example, the proper trajectory of the screw(s) can be determined and they can be placed into the vertebra(e). After locking the screw at the desired angle, the vertebra(e) can be moved (e.g., compressed or distracted) by moving the screw(s) along the rod. When the proper position is attained, the screw(s) can be locked with respect to the rod.

Figure 4A:
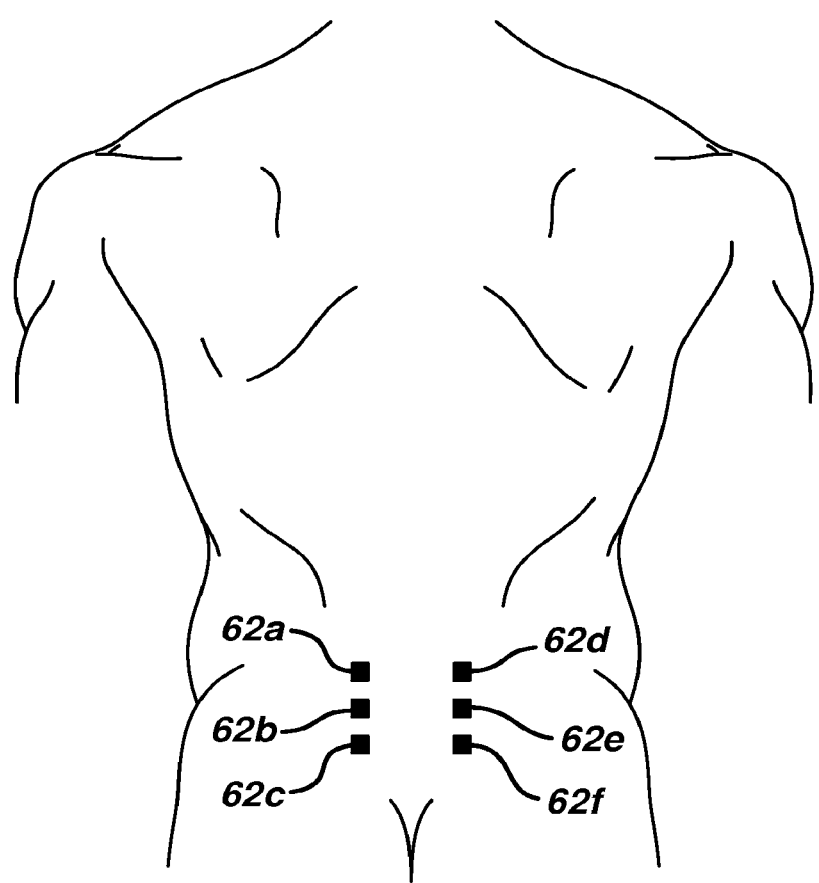
FIG. 4A is a posterior view of six percutaneous incisions formed in the thoracolumbar fascia of a patient's back.

Various techniques can be used to implant the spinal anchors; for example a minimally invasive percutaneous incision may be made through the tissue at one or more of the sites. The location, shape, and size of the incision will depend on the type and quantity of spinal anchors being implanted, as well as the technique being employed to implant the spinal anchors. By way of non-limiting example, FIG. 4A illustrates three midline minimally invasive percutaneous incisions 62a-c formed on one side of three adjacent vertebra in the thoracolumbar fascia in the patient's back, and three additional midline minimally invasive percutaneous incisions 62d-f formed on the opposite side of the three adjacent vertebra in the thoracolumbar fascia in the patient's back. While not shown, a guide system 10, 10' can be positioned adjacent to each set of incisions 62a-c, 62d-f with a targeting member in alignment with each incision.

Figure 4B:
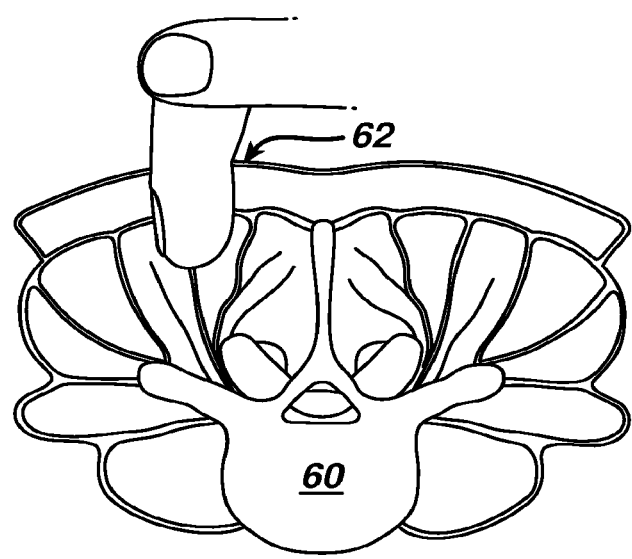
FIG. 4B is an end view showing a blunt dissection of the muscles surrounding a patient's vertebra.

In certain exemplary embodiments, one or more of the incisions may be expanded to create a pathway from the incision to proximate a vertebra. For example, the incision may be expanded by serial dilation, with a retractor such as an expandable retractor, or by any other conventional techniques. In one exemplary embodiment, blunt finger dissection can be used, as shown in FIG. 4B, to separate the longissimus thoracis and multifidus muscles, thereby exposing the facet and the junction of the transverse process and superior articular process.

Figure 4C:
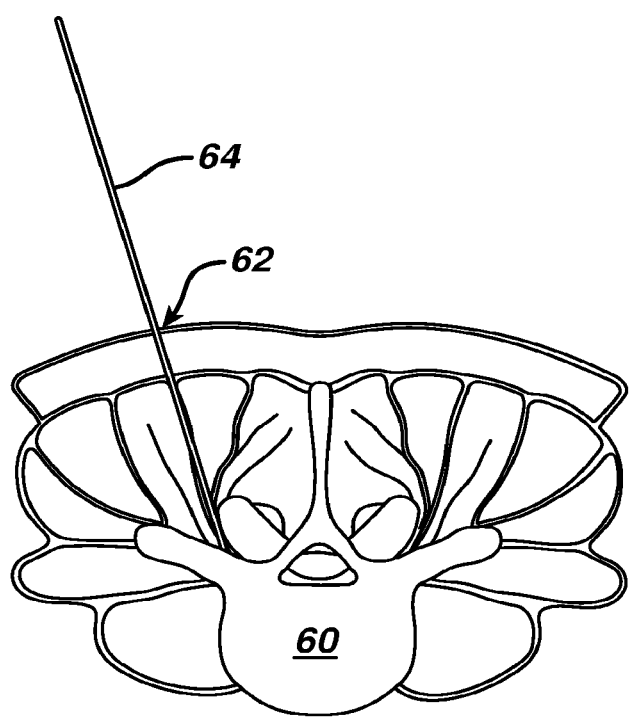
FIG. 4C is an end view of the vertebra in FIG. 4B with a k-wire placed through the incision and into the patient's vertebra.
Figure 4D:
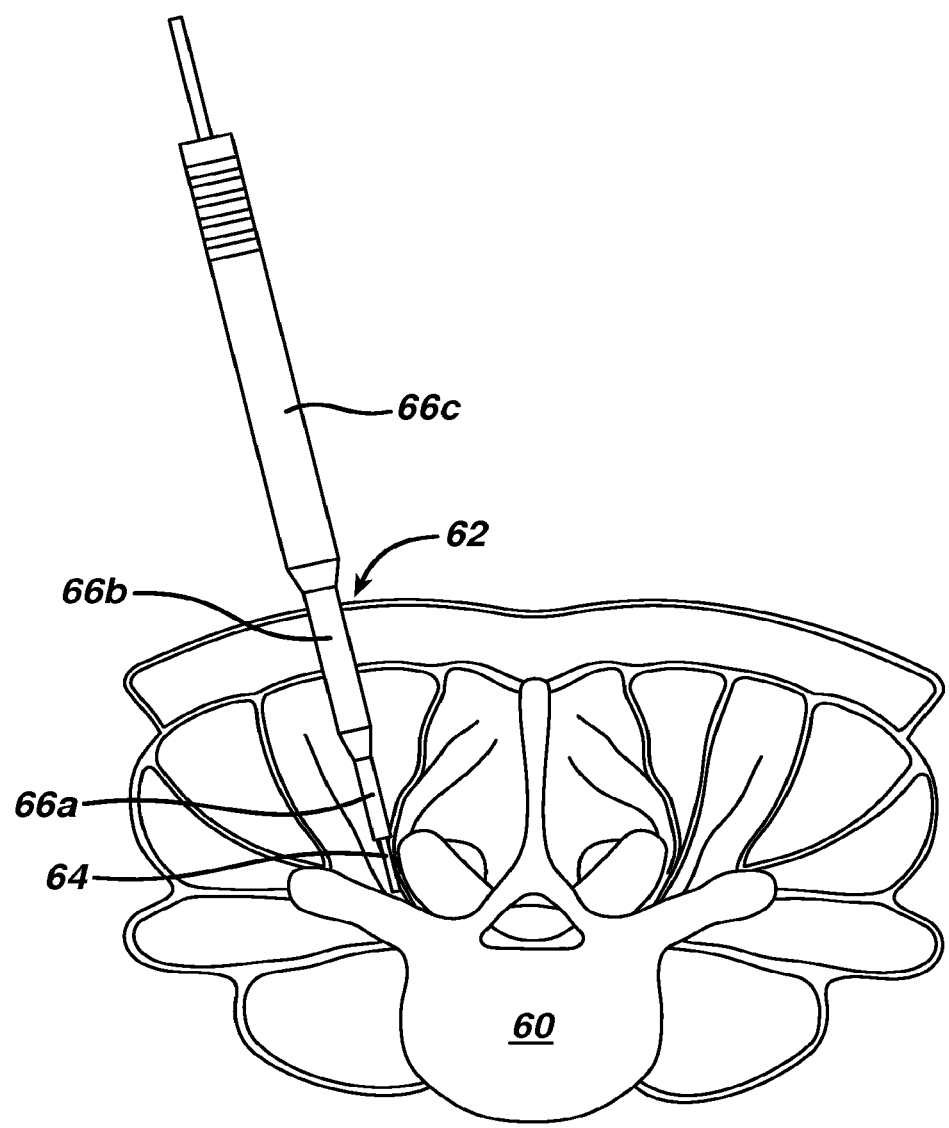
FIG. 4D is an end view of the vertebra in FIG. 4C showing an obturator and several dilators disposed over the k-wire to dilate the tissue and muscles.

A spinal anchor may inserted through one or more of the incisions and the pathways to proximate the vertebra. Any technique for implanting a spinal anchor can be used. In one embodiment, for example, a spinal anchor can be implanted over a guidewire, such as a k-wire. As shown in FIG. 4C, a guide wire, e.g., a k-wire 64, can be implanted, either prior to or after formation of the incision, at each spinal anchor implant site. The k-wire 64 may extend into the vertebra at the desired entry point of the spinal anchor. In certain exemplary embodiments, the k-wire may be advanced into the vertebra. In other exemplary embodiments, the k-wire may be positioned proximate to or against the vertebra. Fluoroscopy or other imaging may be used to facilitate proper placement of the k-wire 64. The incision may be dilated to provide a pathway for delivery of a spinal anchor to each implant site, in the manner discussed above, before or after placement of the guidewire. For example, FIG. 4D illustrates serial dilation at one end of the incision 62 using an obturator 66a having several dilators 66b, 66c of increasing size placed there over. The dilators 66b, 66c are delivered over the obturator 66a and k-wire 64 to essentially stretch the skin around the incision 62 and to expand the pathway to the anchor site. While not shown, the obturator 66a and the dilators 66b, 66c can extend through the targeting members 18a, 18b, 18a', 18b' on the guide system 10, 10', or alternatively the targeting members 18a, 18b, 18a', 18b' can be removed from the guide system 10, 10' and the obturator 66a and dilators 66b, 66c can merely be guided along the k-wire.

One skilled in the art will appreciate that a spinal anchor may be advanced to a vertebra through the incision without the need for a guidewire.

Once the incision 62 is dilated to the proper size, if necessary, the vertebra 60 may be prepared using one or more bone preparation instruments, such as drills, taps, awls, burrs, probes, etc. In certain exemplary embodiments, one or more cannulae can be used to provide a pathway from the incision 62 to the anchor site for insertion of the bone preparation instruments and/or the anchor. In an exemplary embodiment, a relatively small cannula (not shown) may be used to introduce bone preparation instruments into the surgical site. The cannula may be placed through a targeting member 18a, 18b, 18a', 18b' on the guide system 10, 10', such that the cannula is in alignment with the target implant site. Once the vertebra 60 is prepared, a spinal anchor can be delivered along the k-wire, either through the cannula, or after the cannula is removed, and implanted in the vertebra. Alternatively, in embodiments not employing a guidewire, the spinal anchor may be advanced through the incision, e.g., through a cannula, to the vertebra. A cannula, retractor, or other instrument may be employed to guide the spinal anchor to the vertebra.

Figure 5A:
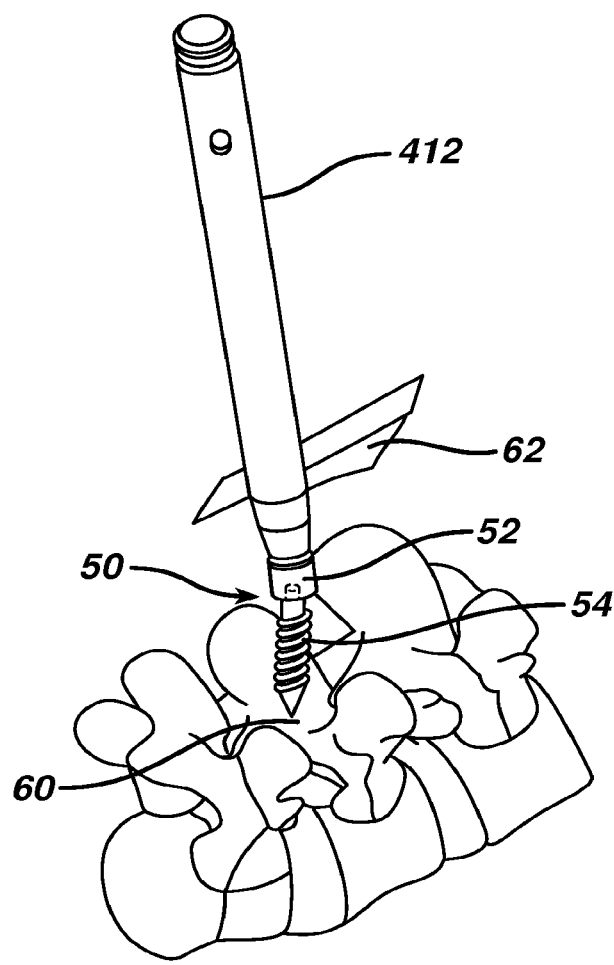
FIG. 5A is perspective view of a first spinal anchor being implanted in a vertebra and having a minimally invasive percutaneous access device coupled thereto and extending through an incision formed in the patient's tissue surface.
Figure 5B:
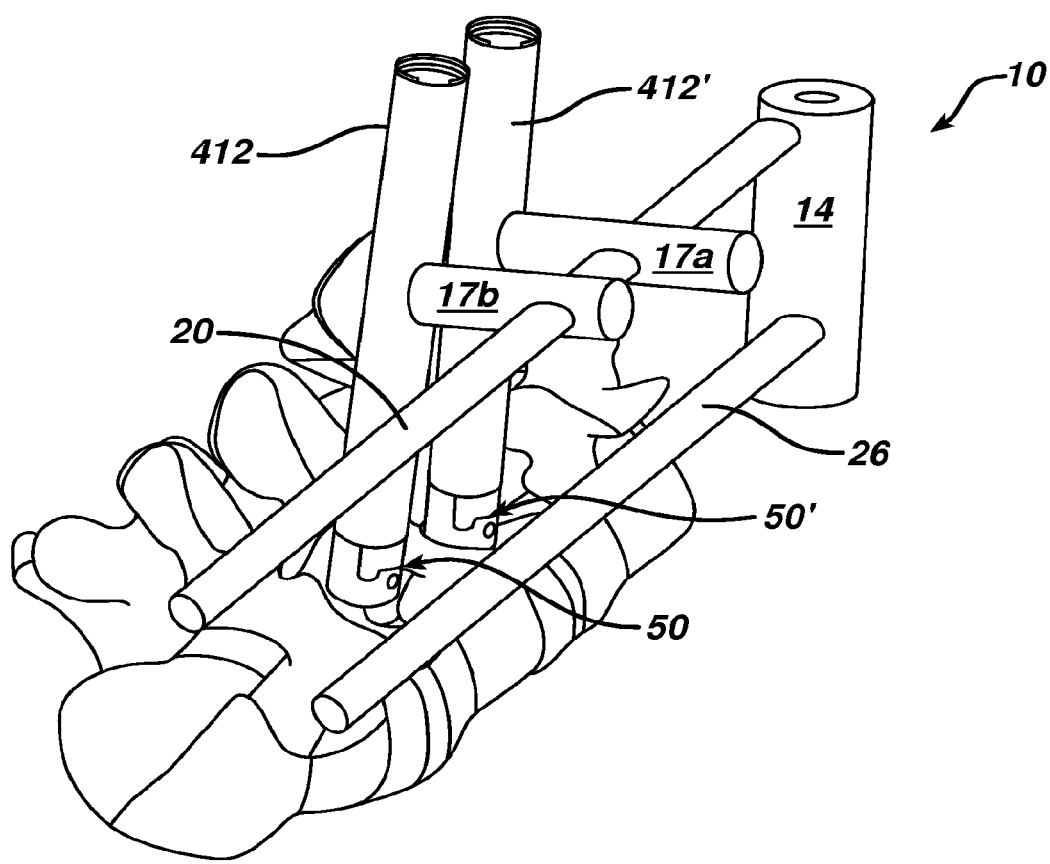
FIG. 5B is a perspective view of the first spinal anchor shown in FIG. 5A implanted in a vertebra and coupled to a first percutaneous access device that is coupled to the guide system shown in FIG. 1, and a second spinal anchor implanted into an adjacent vertebra and coupled to a second percutaneous access device that is coupled to the guide system shown in FIG. 1.

In another embodiment, shown in FIGS. 5A-5B, a spinal anchor can be implanted in the vertebra using a minimally invasive technique. Such a procedure preferably begins by inserting a guidewire, such as a k-wire, through the incision and into the vertebra, dilating the incision to form a pathway, and preparing the vertebra, as discussed above. As shown in FIG. 5A, a minimally invasive percutaneous access device 412, i.e., a cannula, is then inserted through the incision 62, preferably over the k-wire (not shown), to the target implant site on the vertebra (60). A spinal anchor, e.g., spinal screw 50, can be attached to the distal end of the cannula 412, as shown, or the spinal anchor can be passed through the cannula 412 after the cannula 412 is positioned through the incision to extend to the target implant site. In an exemplary embodiment, as shown in FIG. 5B, each access device 412, 412' is attached to a support 17b, 17a, 17b', 17a' on the guide system 10, 10'. While not shown, the access devices can alternatively be inserted through the targeting members 18a, 18b, 18a', 18b' on the guide system 10, 10'. Once the screw 50 is positioned adjacent to the vertebra 60, a driver tool (not shown) can be positioned through the access device 412 and coupled to a receiver head 52 of the spinal screw 50 to drive the screw 50 into the vertebra 60.

This procedure, and other minimally invasive methods and devices for implanting a spinal anchor, are described in more detail in U.S. patent application Ser. No. 10/738,130 of Anderson et al. entitled "Methods And Devices For Minimally Invasive Spinal Fixation Element Placement," U.S. patent application Ser. No. 10/737,537 of Anderson et al. entitled "Methods And Devices For Spinal Fixation Element Placement," and U.S. patent application Ser. No. 10/738,286 filed on Dec. 16, 2003 and entitled "percutaneous access device and bone anchor assembly." These references are incorporated by reference herein in their entirety.

Figure 6A:
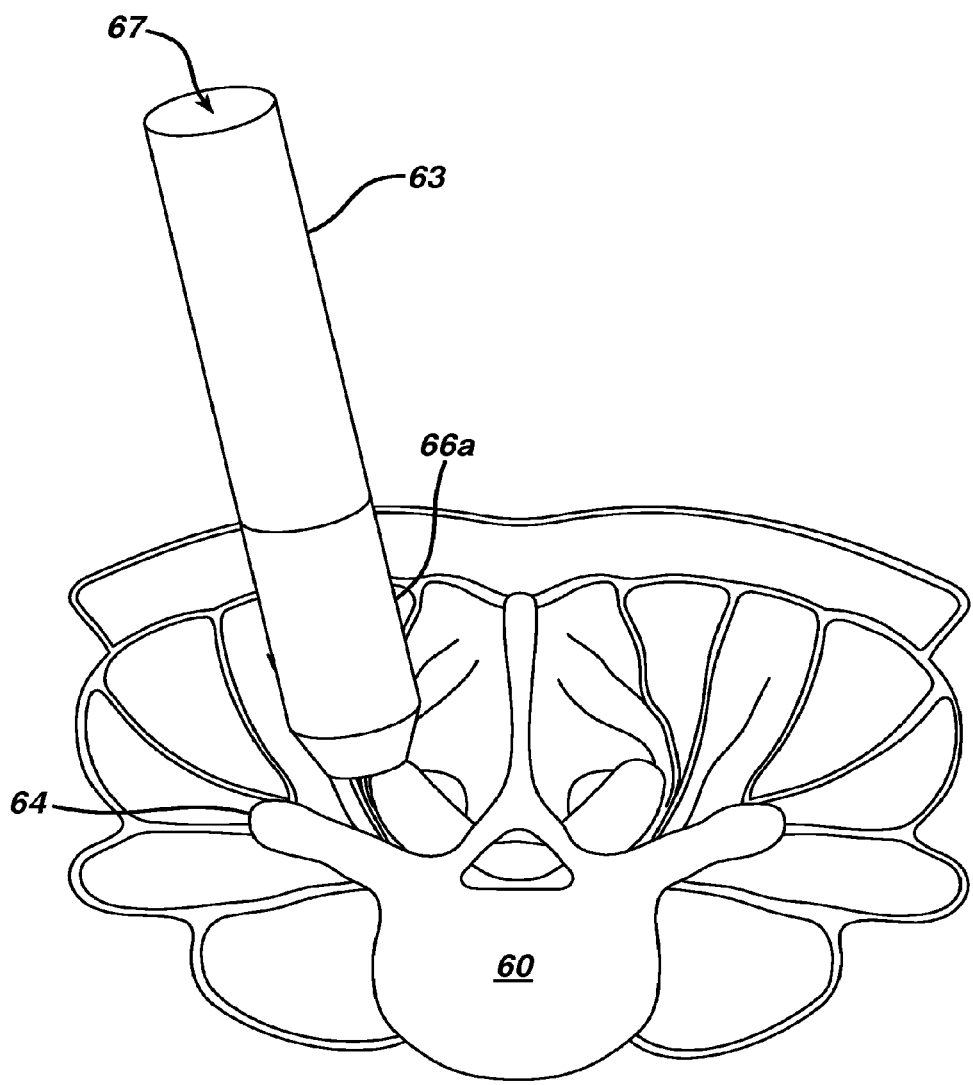
FIG. 6A is an end view of the vertebra in FIG. 4C showing an access port defining a working channel extending to the vertebra.
Figure 6B:
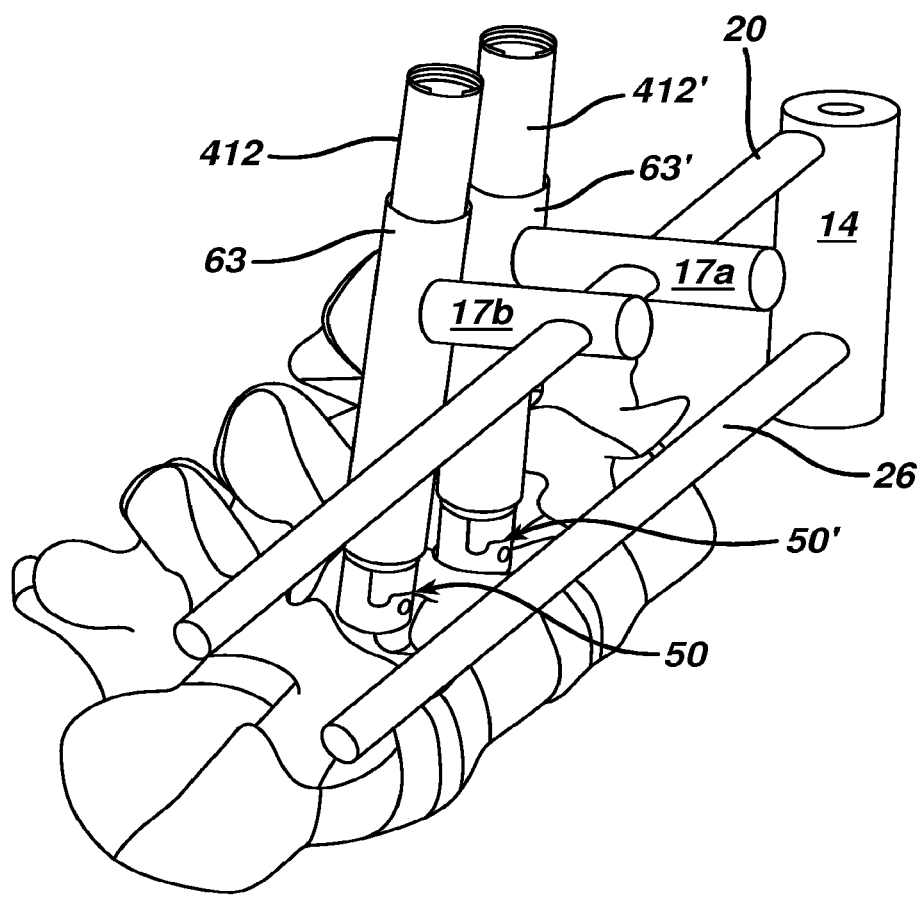
FIG. 6B is a perspective view of the first spinal anchor shown in FIG. 6A implanted in a vertebra and coupled to a first percutaneous access device that extends through a first access port coupled to the guide system shown in FIG. 1, and a second spinal anchor implanted into an adjacent vertebra and coupled to a second percutaneous access device that extends through a second access port coupled to the guide system shown in FIG. 1.

In yet another embodiment, shown in FIGS. 6A-6B, a larger cannula or access port can be used to implant a spinal anchor in each vertebra. Again, as described above, the procedure preferably beings by dilating the incision to form a pathway. The obturator and dilators can optionally be inserted over a k-wire, as also previously described above. Once dilated to the appropriate size, an access port 63 can be inserted over the largest dilator, and the dilators and obturator can be removed such that the access port 63 defines a working channel 67 extending through tissue to the target implant site on the vertebra 60, as shown in FIG. 6A. The vertebra 60 can then be prepared using bone preparing tools and devices. A person skilled in the art will appreciate that the vertebra can be prepared either before dilation, or during dilation using a relatively small cannula, as was also described above. As shown in FIG. 6B, each access port 63, 63' can optionally be mated to a support 17a, 17b, 17a', 17b' on the guide system 10, 10'. While not shown, the access ports 63, 63' can alternatively extend through the targeting members 18a, 18b, 18a', 18b' on the guide system 10, 10'. Once the access port 63 is positioned in relation to the vertebra 60, a spinal anchor can be inserted therethrough and implanted in the vertebra 60. The spinal anchor can optionally be inserted directly through the access port 63, with or without the use of a guide wire (not shown). Or, in another embodiment, shown in FIG. 6B and as previously described above with respect to FIGS. 5A and 5B, each spinal anchor 50, 50' can be implanted using a minimally invasive percutaneous access device 412, 412' coupled thereto.

One skilled in the art will appreciate that a variety of spinal fixation elements can be used with the system described herein. In addition to the spinal fixation elements previously described, FIGS. 7C and 7D illustrate a polyaxial pedicle screw 50' (FIG. 7C) and a monoaxial pedicle screw 50" (FIG. 7D) in association with an insertion guide 19. The polyaxial 50' and monoaxial 50" screws are side-loading, such that the rod 26 can be pulled into an opening in the side of the anchor receiver head 52. In addition, the screws are top-tightening such that the rod can be locked within the receiver head 52 by inserting a locking mechanism 27 (e.g., a set screw) into the top of the receiver head 52, thereby clamping down on the rod.

This embodiment, and other methods for implanting spinal anchors using an access port, are described in more detail in U.S. Pat. No. 6,159,179 of Simonson entitled "Cannula And Sizing And Insertion Method," U.S. Publication No. 2003/0083689 of Simonson entitled "Non Cannulated Dilators," and U.S. Publication No. 2003/0083688 of Simonson entitled "Configured And Sized Cannula." These references are also incorporated by reference herein in their entirety.

A person having ordinary skill in the art will appreciate that the aforementioned methods and devices for implanting spinal anchors can be modified depending on the type of anchor being implanted, as well as the specific procedure being employed. Moreover, other methods and devices known in the art can be used in accordance with the present invention. By way of non-limiting example, U.S. Patent Publication No. 2002/0123668 entitled "Retractor and Method for Spinal Pedicle Screw Placement," and U.S. Patent Publication No. 2003/0236447 entitled "Retractor and Method for Spinal Pedicle Screw Placement," each describe a surgical retractor and methods for spinal anchor placement which can be used with the present invention. These references are incorporated herein in their entirety.

Rod Approximation

Once the spinal anchors are fully implanted in the vertebrae, the spinal rod may be coupled to the anchors. While various techniques can be used to couple the rod to the anchors, in an exemplary embodiment, the rod and/or anchors are approximated toward one another using a lateral approximator device. The lateral approximator device can have virtually any configuration, but it is preferably effective to engage a portion of the anchor and engage the rod, thereby allowing the rod and anchor to be moved toward and coupled to one another.

Figure 7A:
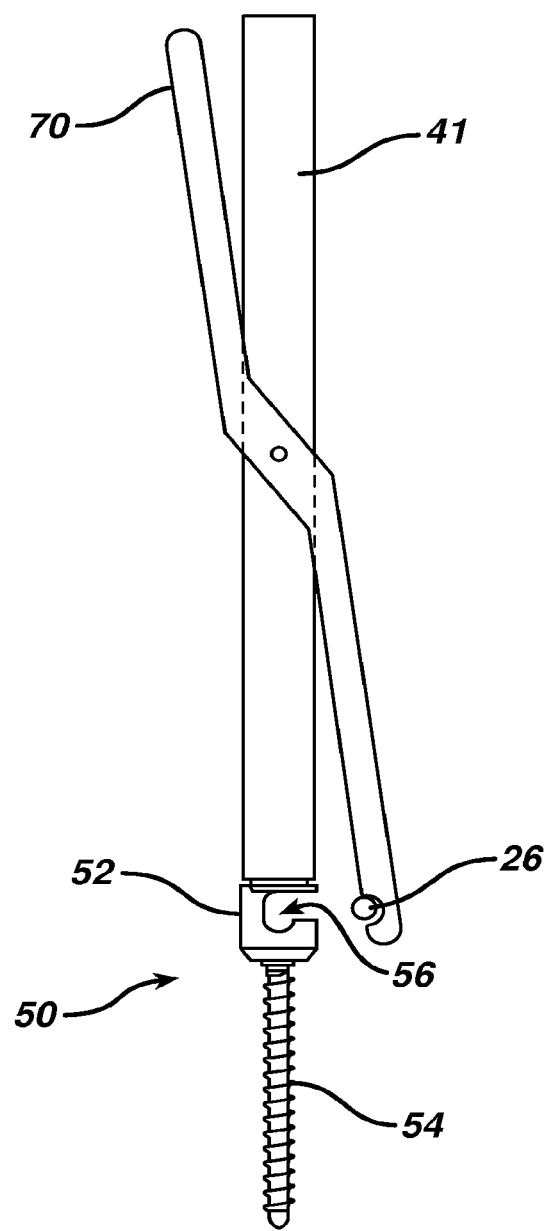
FIG. 7A is a perspective view of an exemplary embodiment of a spinal anchor and a tool for laterally approximating a spinal fixation element toward the spinal anchor.
Figure 7B:
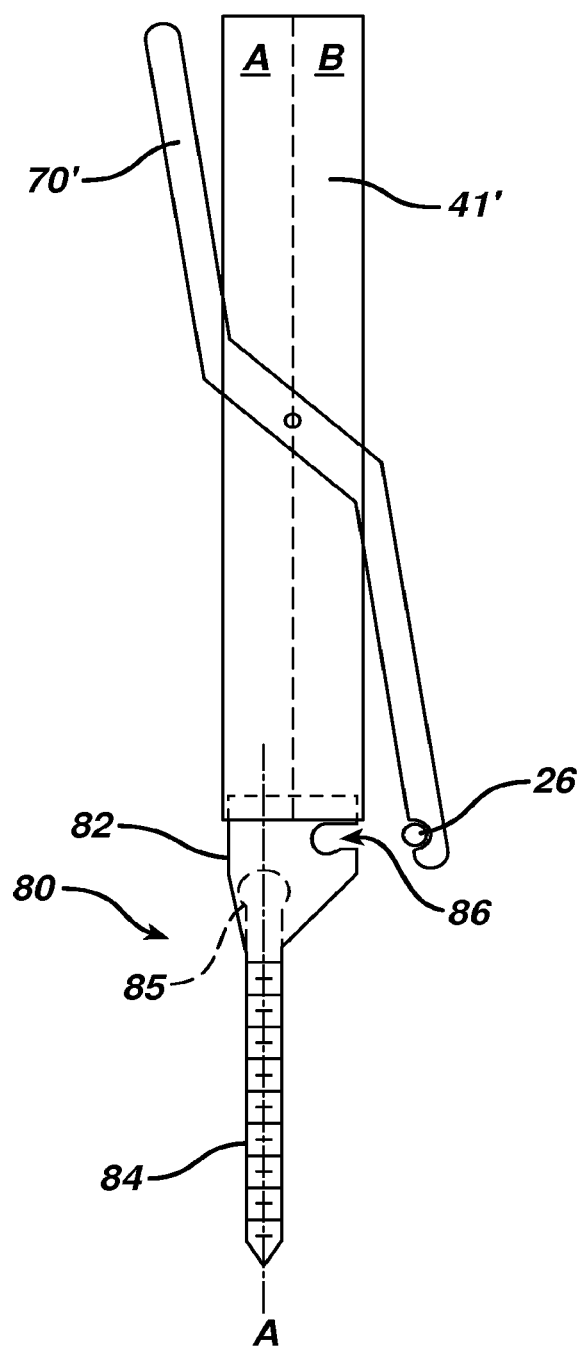
FIG. 7B is a perspective view of another exemplary embodiment of a spinal anchor and a tool for laterally approximating a spinal fixation element toward the spinal anchor.
Figure 7C:
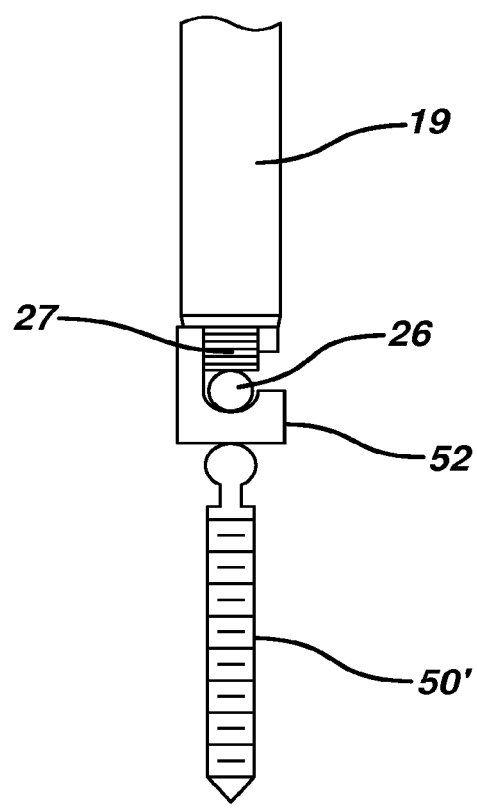
FIG. 7C is an exploded view of an exemplary polyaxial spinal fixation element with an insertion guide.
Figure 7D:
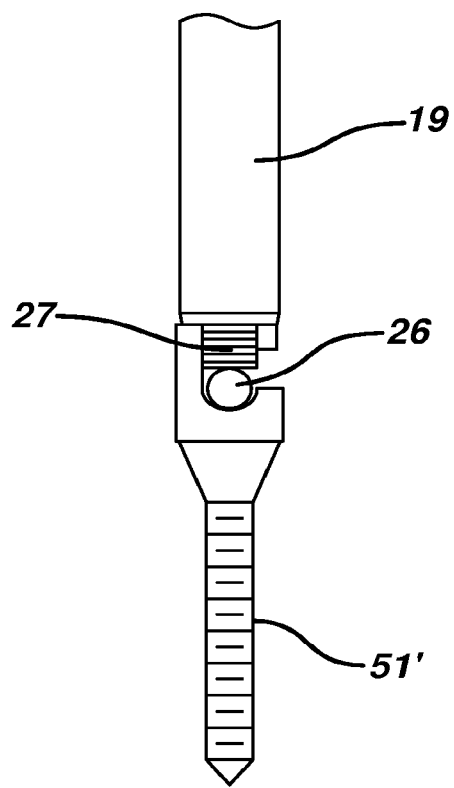
FIG. 7D is a side, view, partially cutaway, of an exemplary monoaxial spinal fixation element with an insertion guide.

FIGS. 7A and 7B illustrate exemplary embodiments of a lateral approximator device 70, 70' that is effective to couple to an anchor 50, 80 and to engage a rod 26, 26' to pull the anchor 50, 80 and/or rod 26, 26' toward one another until the rod 26, 26' is seated within the side opening 56, 86 in the receiver head 52, 82 of the anchor 50, 80. More particularly, the device 70, 70' is in the form a pivoting arm that is coupled to an elongate tubular member, such as a cannula 41, 41'. In one embodiment, the cannula 41, 41' can be adapted to attach to the anchor 50, 80 or to fit over a cannula attached to the anchor 50, 80. In another embodiment, the cannula 41, 41' can be the percutaneous access device 412 shown in FIG. 5A, and the lateral approximator device 70, 70' can be removably matable to the access device 412. In yet another embodiment, the cannula 41, 41' can include one or more lumens formed therethrough for guiding tools and devices to the anchor 50, 80. For example, the lateral approximator device 70 shown in FIG. 7A only includes a single lumen formed therein for receiving a driver tool and a first locking mechanism, such as a set screw, for locking the receiving head 52 relative to the shank 54, and for receiving a driver tool and a second locking mechanism, such as a set screw, for locking the rod 26, 26' within the receiver head 52. The lateral approximator device 80 shown in FIG. 7B, on the other hand, is bifurcated and includes first and second lumens A, B formed therein for allowing a first locking mechanism, such as a set screw, to be delivered through the first lumen A to lock the receiver head 82 to the shank 84, while a second locking mechanism, such as a set screw, is delivered separately through the second lumen B to lock the rod 26, 26' relative to the receiver head 82. Regardless of the configuration of the cannula 41, 41', the lateral approximator 70, 70' should be effective to pivot relative to the cannula 41, 41' to engage a rod 26, 26' and pull the rod 26, 26' and/or anchor 50, 80 toward one another.

Figure 8:
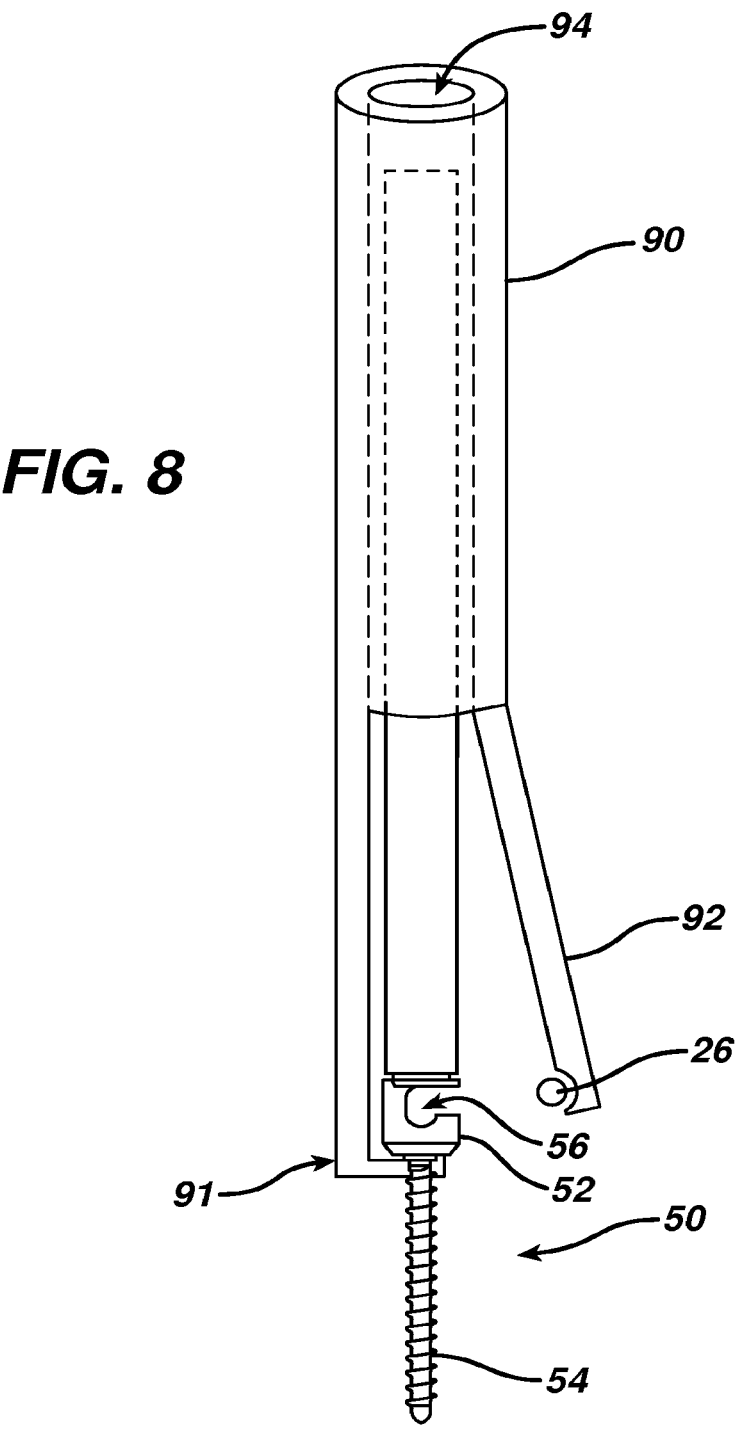
FIG. 8 is a transparent perspective view of another exemplary embodiment of a tool for laterally approximating a spinal fixation element toward a spinal anchor.

FIG. 8 illustrates another embodiment of a lateral approximator device 90. In this embodiment, the device 90 is in the form of a cannula having an inner lumen 94 extending therethrough and having a pivoting arm 92 formed thereon or coupled thereto. The distal end 91 of the device 90 is effective to engage the receiver head 52 of a spinal anchor 50, and the pivoting arm 92 is effective to pivot to engage a spinal rod 26, 26' to pull the rod 26, 26' into the side-opening 56 in the receiver head 52.

A person skilled in the art will appreciate that a variety of other techniques can be used to couple a spinal rod to the spinal anchors. Moreover, the spinal rod does not need to be directly attached to each anchor, and it can be indirectly attached to the anchors using, for example, a band clamp, or slotted or offset connectors. Once the spinal rod is fully seated in the receiver head of each spinal anchor, a closure mechanism can be applied to each receiver head to retain the spinal rod therein.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A method for implanting a spinal fixation system, comprising:
providing a guide system having
a guide member having a rod-engaging portion disposed at a terminal end of the guide member, and
a targeting element movably coupled to the guide member;
coupling a spinal fixation element to the rod-engaging portion of the guide member such that the spinal fixation element is held by the rod-engaging portion at a location that is remote from locations accessible by the targeting element along a longitudinal axis of the spinal fixation element, the spinal fixation element being held in a fixed position in a patient's body, and being held such that the spinal fixation element is substantially parallel to the guide member;

after the spinal fixation element is in the fixed position in the patient's body, manipulating the targeting element to target an implant site on a vertebra at a location that is offset from the spinal fixation element; and coupling the spinal fixation element that is maintained by the rod-engaging portion of the guide member to at least one spinal anchor implanted at the implant site.

2. The method of claim 1, wherein the spinal fixation element is removably mated to the rod-engaging portion by a locking mechanism.

3. The method of claim 1, further comprising placing an imaging device over the targeting element to align the targeting element with the implant site.

4. A method for implanting a spinal fixation system, comprising:
   providing a guide system having
      a guide member having a rod-engaging portion disposed at a terminal end of the guide member, and
      a targeting element movably coupled to the guide member;
   coupling a spinal fixation element to the rod-engaging portion of the guide member such that the spinal fixation element is held in a fixed position in a patient's body by the rod-engaging portion, and such that the spinal fixation element is substantially parallel to the guide member;
   after the spinal fixation element is in the fixed position in the patient's body, manipulating the targeting element to target an implant site on a vertebra at a location that is offset from the spinal fixation element;
   coupling the spinal fixation element that is maintained by the rod-engaging portion of the guide member to at least one spinal anchor implanted at the implant site; and
   sliding the targeting element along a length of the guide member.

5. The method of claim 4, wherein the spinal fixation element is removably mated to the rod-engaging portion by a locking mechanism.

6. The method of claim 4, further comprising placing an imaging device over the targeting element to align the targeting element with the implant site.

7. The method of claim 4, further comprising inserting the spinal fixation element into the patient's body in a first orientation and pivoting the spinal fixation element into a second orientation in which the spinal fixation element is substantially parallel to a longitudinal axis of the guide member, the longitudinal axis of the guide member extending substantially parallel to the patient's spinal column.

8. The method of claim 4, further comprising pulling the spinal fixation element toward the at least one spinal anchor using a grasping tool.

9. A method for implanting a spinal fixation system, comprising:
   providing a guide system having
      a guide portion having a length and a width, the length being greater than the width and extending from a first end to a second end, and the guide portion further having an axis extending along the length of the guide portion,
      a rod-engaging member mated to the guide portion at one of the first or second ends, the rod-engaging member having an axis that is fixedly and substantially transverse to the axis of the guide portion, and
      at least one targeting member slidably coupled to the guide portion;
   positioning the guide portion outside a patient's body such that the length of the guide portion extends along the patient's spinal column;
   coupling a spinal rod to the rod-engaging member such that the rod-engaging member maintains the spinal rod in a fixed position within the patient's body, the spinal rod being spaced a distance apart from the guide portion and substantially parallel to the guide portion;
   targeting an implant site using the at least one targeting member; and
   coupling the spinal rod to at least one spinal anchor implanted at the implant site.

10. The method of claim 9, wherein the at least one targeting member is removably coupled to a support member slidably disposed on the guide portion.

11. The method of claim 9, wherein the spinal rod is removably mated to the rod-engaging member by a locking mechanism.

12. The method of claim 9, further comprising, prior to coupling the spinal rod to the rod-engaging member, inserting the spinal rod into the patient's body in a first orientation and pivoting the spinal rod into a second orientation in which the spinal rod is substantially parallel to the guide portion.

13. The method of claim 12, wherein an insertion tool performs the inserting and pivoting of the spinal rod, the insertion tool including a sloped guide member disposed at a distal end thereof.

14. The method of claim 9, wherein the at least one spinal anchor comprises a side-loading, top-tightening spinal anchor.

15. The method of claim 9, further comprising aligning the at least one targeting member with the implant site using an imaging device placed over at least one of the at least one targeting members.

16. The method of claim 9, further comprising pulling the spinal rod toward the at least one spinal anchor using a grasping tool.

17. The method of claim 9, wherein the method includes performing serial dilation with a series of dilators to form an enlarged working channel that extends from a skin surface to the implant site.

18. The method of claim 17, further comprising positioning a cannula over the series of dilators and removing the series of dilators such that the cannula defines the enlarged working channel extending therethrough.

19. The method of claim 9, wherein the at least one targeting member includes an opening disposed therethrough that is laterally offset from the guide portion.

* * * * *